United States Patent [19]

Hahnen

[11] Patent Number: 5,569,244
[45] Date of Patent: Oct. 29, 1996

[54] LOOP ELECTRODES FOR ELECTROCAUTERY PROBES FOR USE WITH A RESECTOSCOPE

[75] Inventor: Kevin F. Hahnen, Cooper City, Fla.

[73] Assignee: Symbiosis Corporation, Miami, Fla.

[21] Appl. No.: 425,386

[22] Filed: Apr. 20, 1995

[51] Int. Cl.⁶ .................................................. A61B 17/39
[52] U.S. Cl. ..................................... 606/46; 606/49
[58] Field of Search ............................ 606/45, 46, 49, 606/160; 128/757

[56] References Cited

U.S. PATENT DOCUMENTS

| | | | |
|---|---|---|---|
| 1,930,214 | 10/1933 | Wappler .................................... | 174/89 |
| 1,963,636 | 6/1934 | Wappler . | |
| 1,971,024 | 8/1934 | Wappler .................................... | 174/89 |
| 2,002,594 | 5/1935 | Wappler et al. ........................... | 174/89 |
| 2,004,559 | 6/1935 | Wappler et al. ........................... | 174/89 |
| 2,011,169 | 8/1935 | Wappler .................................... | 174/89 |
| 2,090,923 | 8/1937 | Wappler .............................. | 128/303.15 |
| 2,224,464 | 12/1940 | Wolf .................................... | 128/303.14 |
| 2,484,059 | 10/1949 | Wallace .............................. | 128/303.15 |
| 2,487,502 | 11/1949 | Willinsky ........................... | 128/303.14 |
| 2,815,757 | 12/1957 | Piar .................................... | 128/303.14 |
| 3,149,633 | 9/1964 | Zingale .............................. | 128/303.15 |
| 3,752,159 | 8/1973 | Wappler ............................. | 128/303.15 |
| 3,856,015 | 12/1974 | Iglesias .............................. | 128/303.15 |
| 3,973,568 | 8/1976 | Iglesias .............................. | 128/303.15 |
| 3,990,456 | 11/1976 | Iglesias .............................. | 128/303.15 |
| 4,060,087 | 11/1977 | Hiltebrandt et al. ............... | 128/303.15 |
| 4,116,198 | 9/1978 | Roos .................................. | 128/303.15 |
| 4,134,406 | 1/1979 | Iglesias .............................. | 128/303.15 |
| 4,149,538 | 4/1979 | Mrava et al. . | |
| 4,362,160 | 12/1982 | Hiltebrandt ....................... | 128/303.15 |
| 4,506,668 | 3/1985 | Konig ................................ | 128/303.15 |
| 4,649,917 | 3/1987 | Karasawa .......................... | 128/303.14 |
| 4,657,018 | 4/1987 | Hakky ............................... | 128/303.15 |
| 4,726,370 | 2/1988 | Karasawa et al. ................. | 128/303.15 |
| 4,917,082 | 4/1990 | Grossi et al. ........................... | 606/46 |
| 5,007,907 | 4/1991 | Nishigaki et al. ..................... | 606/46 |
| 5,064,424 | 11/1991 | Bitrolf .................................... | 606/46 |
| 5,080,660 | 1/1992 | Buelna .................................... | 606/45 |
| 5,196,011 | 3/1993 | Korth et al. ............................ | 606/46 |
| 5,201,741 | 4/1993 | Dulebohn ............................. | 606/113 |
| 5,318,564 | 6/1994 | Eggers .................................... | 606/47 |
| 5,324,288 | 6/1994 | Billings et al. ......................... | 606/45 |
| 5,342,357 | 8/1994 | Nardella ................................ | 606/40 |
| 5,354,296 | 10/1994 | Turkel .................................... | 606/41 |
| 5,374,188 | 12/1994 | Frank et al. ............................ | 433/32 |
| 5,376,087 | 12/1994 | Haber et al. .......................... | 606/27 |
| 5,395,312 | 3/1995 | Desai ..................................... | 604/22 |
| 5,395,363 | 3/1995 | Billings et al. ......................... | 606/41 |
| 5,395,368 | 3/1995 | Ellman et al. ......................... | 606/45 |
| 5,397,320 | 3/1995 | Essig et al. ............................. | 606/37 |

FOREIGN PATENT DOCUMENTS 3707403   9/1987   Germany ................................ 606/46

*Primary Examiner*—Lee S. Cohen
*Attorney, Agent, or Firm*—David P. Gordon

[57] ABSTRACT

An electrocautery probe includes a distal loop electrode mounted between a pair of arms which are joined at their proximal ends to an electrode lead, and a mounting sleeve for slideably coupling the probe to the guide tube of a resectoscope. The loop electrode is formed with a relatively broad lower surface defining a sharp distal edge and a sharp proximal edge. The electrode may have a triangular cross section or a cross section which is defined by an upper convex surface and a lower flat surface. A presently preferred embodiment of the electrode has a triangular cross section with a lower base surface approximately 0.039–0.043 inches wide, a distal upper surface extending approximately 0.018–0.022 inches from the base, and a proximal upper surface which extends approximately 0.063–0.067 inches from the distal upper surface to the lower base surface. The electrode thereby defines a sharp distal edge having an angle of approximately 95°, and a sharp proximal edge having an angle of approximately 30°. The electrode is preferably made of chromium cobalt or carbonless stainless steel. Tests have demonstrated that the electrode according to the invention is approximately 90% more effective in coagulation than the known loop electrodes. It is believed that the sharp distal and proximal edges aid in cutting and focus cautery current to this effect while the relatively broad base serves to enhance coagulation.

24 Claims, 3 Drawing Sheets

LOOP ELECTRODES FOR ELECTROCAUTERY PROBES FOR USE WITH A RESECTOSCOPE

BACKGROUND OF THE INVENTION

1. Field of the Invention

This invention relates broadly to endoscopic instruments. More particularly, this invention relates to loop electrodes which are used in electrocautery probes with a resectoscope.

2. State of the Art

Electrosurgical resection is a procedure in which damaged or enlarged tissue is excised with an electrocautery probe. Transurethral resection is an electrosurgical procedure in which a portion of the prostrate is excised by means of an instrument passed through the urethra. Endometrial ablation is an electrosurgical alternative procedure to hysterectomy for women with menorrhagia (abnormal or excessive uterine bleeding). In both procedures, the instrument typically used is called a resectoscope or hysteroscope. Prior art FIG. 1 shows a typical resectoscope 10 with an electrocautery probe 12. The resectoscope 10 includes a distal guide tube 14 and a proximal handle 16. A telescope 18 is inserted through the guide tube 14 and is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24 which is coupled to a source of cautery current (not shown). A mounting sleeve 29 is provided on the probe 12 for slideably coupling it to the guide tube 14. The mounting sleeve 29 is typically located at the point where the arms 23, 25 are joined to the electrode lead 27. The handle 16 is generally capable of axially sliding the probe 12 and its distally mounted electrode 22 relative to the guide tube 14.

The resection procedure involves applying a cauterizing voltage to the electrode 22 and moving the electrode slowly through or over the prostate or endometrium while viewing the tissue through the scope 18. Thermal energy is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a puncrate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

The loop electrode 22, which is shown in FIGS. 1 and 2 is the presently preferred type of electrode for prostatic resection because it can be used to cut and to coagulate. The disadvantage of the loop electrode is that in order to make the electrode sharp enough to cut, it must be made relatively thin with little surface area. The small surface area of the loop electrode compromises its effectiveness as a coagulating tool. Thus, in a prostatic resection procedure, 80% of the time devoted to the procedure is used to coagulate the prostate and stop it from bleeding.

SUMMARY OF THE INVENTION

It is therefore an object of the invention to provide an electrocautery probe with a loop electrode which is useful for cutting and for coagulating.

It is also an object of the invention to provide an electrocautery probe with a loop electrode which is relatively sharp.

It is another object of the invention to provide an electrocautery probe with a loop electrode which has an increased surface area for better coagulation.

It is still another object of the invention to provide an electrocautery probe with a loop electrode which has two sharp edges, one for plunging and another for scything.

In accord with these objects which will be discussed in detail below, the electrocautery probe of the present invention includes a distal loop electrode mounted between a pair of arms which are joined at their proximal ends to an electrode lead, and a mounting sleeve for slideably coupling the probe to the guide tube of a resectoscope. According to the invention, the loop electrode is formed with a relatively broad lower surface defining a sharp distal edge and a sharp proximal edge. The electrode may have a triangular cross section or a cross section which is defined by an upper convex surface and a lower substantially flat surface. A presently preferred embodiment of the electrode has a triangular cross section with a lower base surface approximately 0.039 to 0.043 inches wide, a distal surface extending approximately 0.018 to 0.022 inches from the base, and a proximal upper surface which extends approximately 0.063 to 0.067 inches from the distal surface to the lower base surface. The electrode thereby defines a sharp distal edge having an angle of approximately 95°, and a sharp proximal edge having an angle of approximately 30°. The electrode is preferably made of chromium cobalt or carbonless stainless steel. Tests have demonstrated that the electrode according to the invention is approximately 90% more effective in coagulation than the prior art loop electrodes. It is believed that the sharp distal and proximal edges aid in cutting and focus cautery current to this effect while the relatively broad base serves to enhance coagulation.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
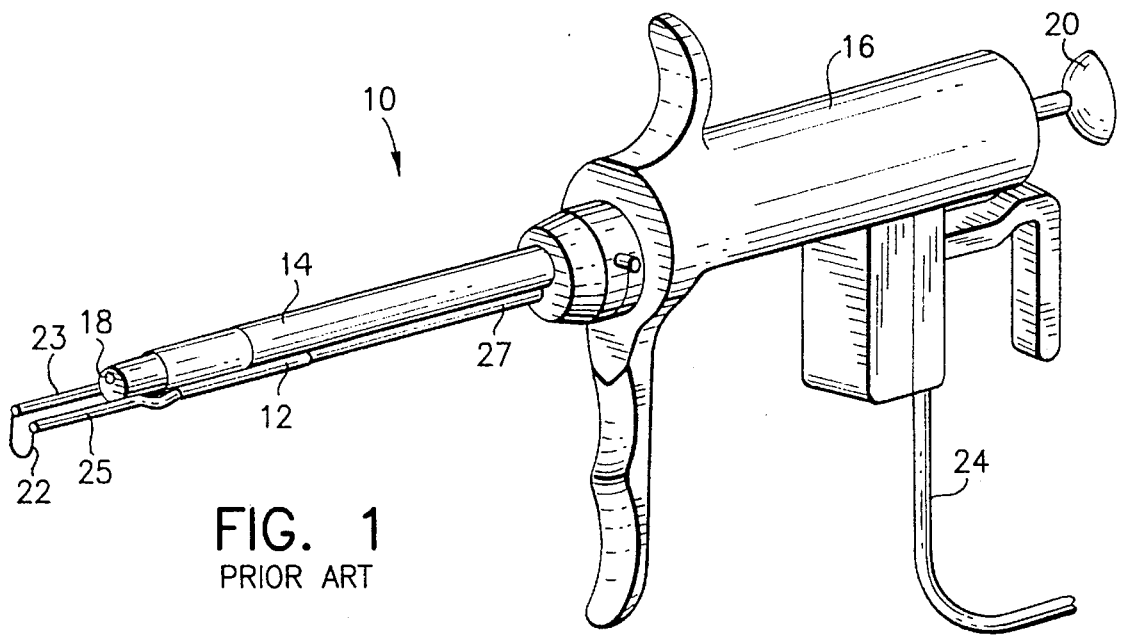
FIG. 1 is a perspective view of a prior art resectoscope with an electrocautery probe having a loop electrode.
Figure 2:
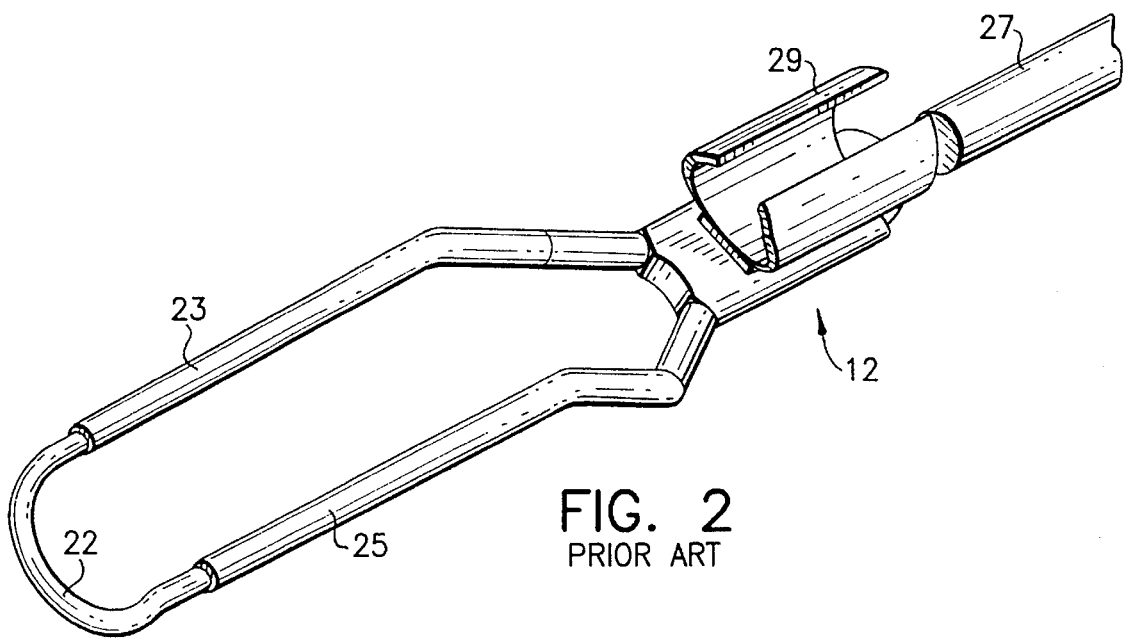
FIG. 2 is an enlarged broken perspective view of the prior art electrocautery probe of FIG. 1.
Figure 3:
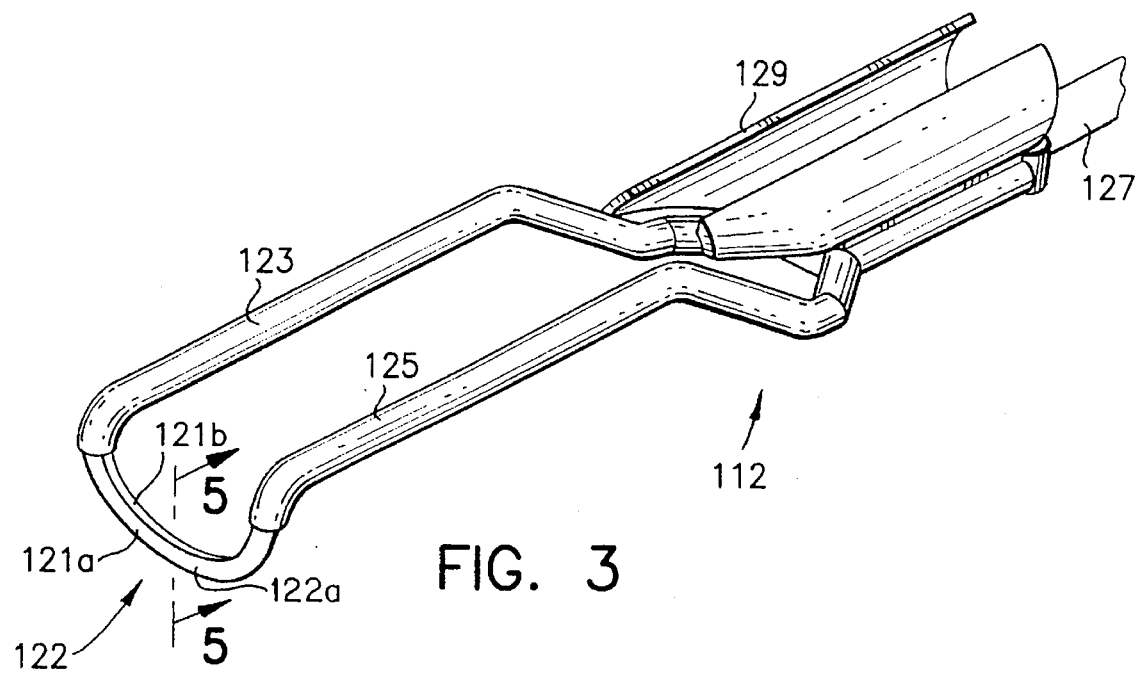
FIG. 3 is an enlarged broken perspective view of the distal end of an electrocautery probe according to the invention.
Figure 4:
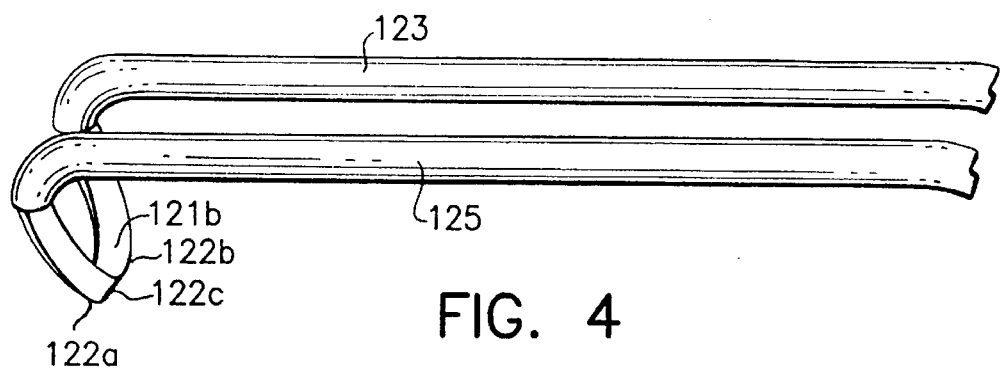
FIG. 4 is a view similar to FIG. 3 showing the proximal side of an electrode according to the invention.
Figure 5:
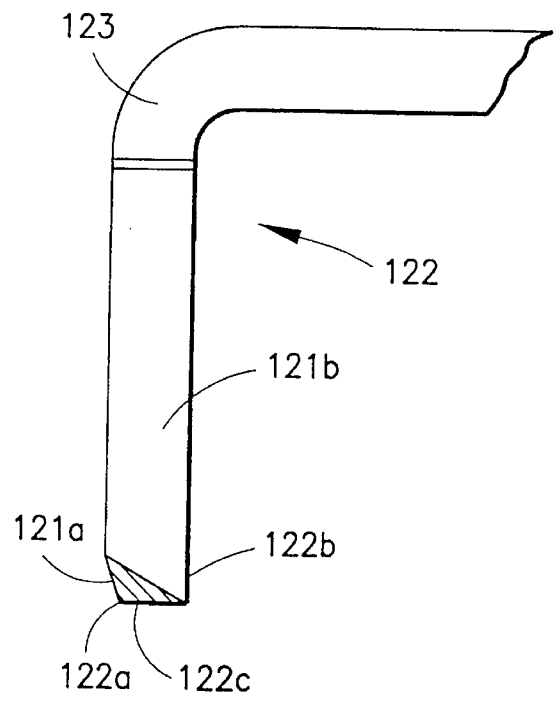
FIG. 5 is a cross sectional view taken along line 5—5 in FIG. 3.

Referring now to FIGS. 3 through 5, a cautery probe 112 according to the invention has a distal electrode 122 which is mounted between a pair of arms 123, 125. The arms 123, 125 are joined at their proximal ends to an electrode lead 127 and a resectoscope mounting sleeve 129 is provided preferably at the location where the arms 123, 125 are joined to the electrode lead 127. The electrode 122 according to the invention is a substantially U-shaped loop coupled by its upper ends to the distal ends of the arms 123, 125, and having a cross section which defines a sharp distal edge 122a, a sharp proximal edge 122b, and a lower base surface 122c. The overall height of the electrode 122 is typically approximately 0.170 inches.

According to a first embodiment of the invention, the electrode 122 has a triangular cross section which is seen best in FIG. 5. The triangular cross section is defined by three surfaces: the aforementioned lower base surface 122c, a distal surface 121a and a proximal or upper surface 121b. According to a presently preferred embodiment of the invention, the lower base surface 122c is approximately 0.039–0.043 inches wide, the distal surface 121a extends approximately 0.018–0.022 inches from the base surface, and the proximal upper surface extends approximately 0.063–0.067 inches from the distal surface to the lower base surface. The electrode thereby defines a sharp distal edge 122a having an angle of approximately 95°, and a sharp proximal edge 122b having an angle of approximately 30°. In the presently preferred embodiment, the electrode 122 is coupled to the arms 123, 125 so that the distal surface 121a of the electrode lies in a plane which is angled approximately 10° proximally relative to a plane substantially perpendicular to the arms 123, 125. The electrode is preferably made of chromium cobalt or carbonless stainless steel. From the foregoing, it will be appreciated that the cross section of the electrode 122 shown in FIG. 5 defines a slightly obtuse triangle. Tests of this electrode demonstrated superior cutting and coagulation as compared to the prior art loop electrodes. It should be noted that the sharp edges 122a, 122b need not be (and preferably are not) "cutting sharp". The electrode cuts with the assistance of the cautery current passing through it. It is believed that the sharp edges provide well-defined lines of focus for the cautery current and thereby improve the cutting ability of the electrode. It is also believed that the broad lower surface 122c provides the additional surface area which enhances coagulation. Therefore, it is believed that the most important features of the invention are to provide at least one well-defined edge for cutting and to provide a relatively broad substantially flat surface for coagulating.

Figure 5A:
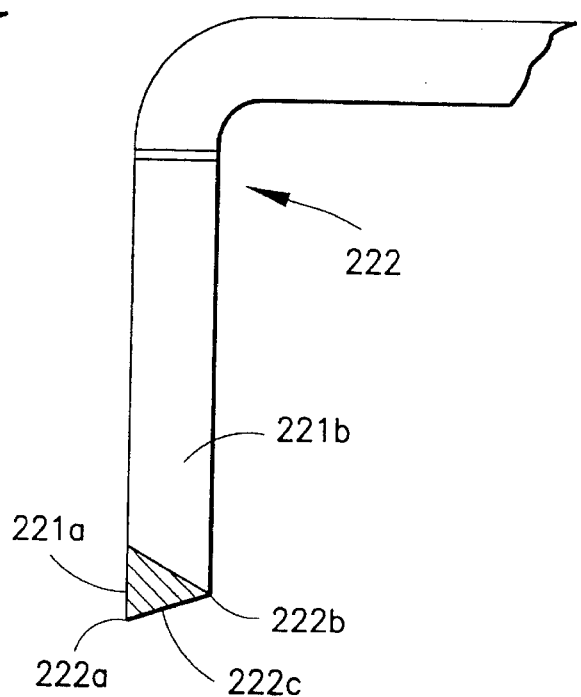
FIG. 5a is a view similar to FIG. 5 of a second embodiment of the electrode according to the invention.
Figure 5C:
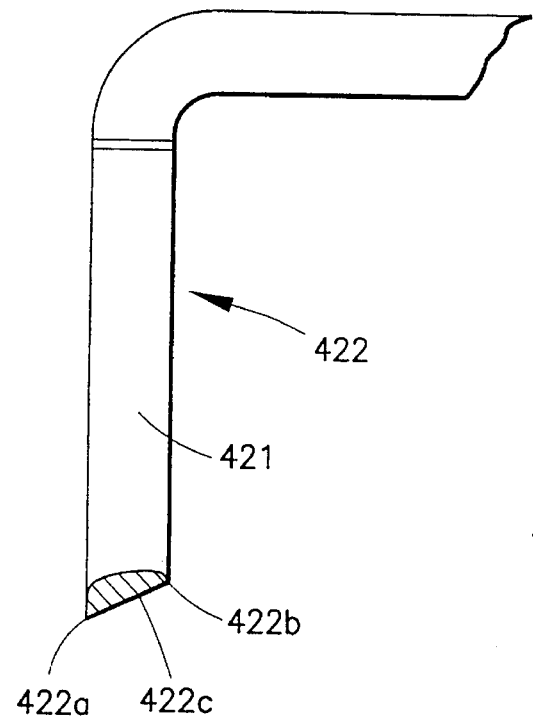
FIG. 5c is a view similar to FIG. 5 of a fourth embodiment of the electrode according to the invention.
Figure 5B:
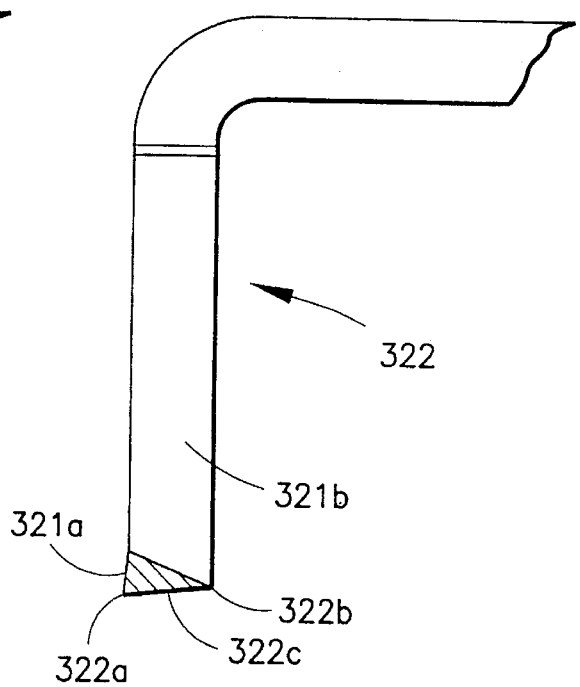
FIG. 5b is a view similar to FIG. 5 of a third embodiment of the electrode according to the invention.

In view of the above, it will be appreciated that the objects of the invention can be achieved with an electrode having a slightly different cross section from the one described above. For example, while the above described electrode has a cross section defining an obtuse triangle, the electrode 222 shown in FIG. 5a has a cross section defining an acute triangle. Nevertheless, the electrode 222 has a sharp distal edge 222a, a sharp proximal edge 222b, and a broad lower surface 222c. Similarly, the electrode 322 shown in FIG. 5b has a cross section defining a right triangle. Nevertheless, the electrode 322 has a sharp distal edge 322a, a sharp proximal edge 322b, and a broad lower surface 322c.

From the foregoing, it will further be appreciated that the objects of the invention can also be achieved with an electrode having a non-triangular cross section. For example, the electrode 422 shown in FIG. 5c has a cross section which is defined by a substantially flat lower surface 422c and a convex upper surface 421. Nevertheless, the electrode 422 has a sharp (i.e. angled as opposed to rounded) distal edge 422a, a sharp proximal edge 422b, and a broad lower surface 422c.

There have been described and illustrated herein several embodiments of a loop electrode. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while a particular electrocautery probe has been shown in connection with the electrode, it will be recognized that other types of probes could be used with similar results obtained. Moreover, while the electrode and probe have been disclosed as having particular utility in connection with a resectoscope, it will be understood that desirable results can be achieved by the electrode without the use of a resectoscope. It will therefore be appreciated by those skilled in the art that yet other modifications could be made to the provided invention without deviating from its spirit and scope as so claimed.

I claim:

1. A loop electrode for use in an electrocautery probe having two arms between which said electrode is mounted, said electrode comprising:

a substantially U-shaped conductive member having a cross section defining at least one sharp edge and a substantially flat lower surface.

2. A loop electrode according to claim 1, wherein:

said cross section defines a sharp distal edge and a sharp proximal edge.

3. A loop electrode according to claim 2, wherein:

said cross section is substantially triangular.

4. A loop electrode according to claim 3, wherein:

said cross section is defined by a distal surface, a proximal surface, and said substantially flat lower surface, said lower surface extending approximately 0.039–0.043 inches between said distal surface and said proximal surface.

5. A loop electrode according to claim 4, wherein:

said distal surface extends approximately 0.018–0.022 inches between said lower surface and said proximal surface.

6. A loop electrode according to claim 5, wherein:

said proximal surface extends approximately 0.063–067 inches between said distal surface and said lower surface.

7. A loop electrode according to claim 3, wherein:

said substantially triangular cross section defines an acute triangle.

8. A loop electrode according to claim 3, wherein:

said substantially triangular cross section defines an obtuse triangle.

9. A loop electrode according to claim 3, wherein:

the two arms of the probe lie in a first plane;

said cross section is defined by a distal surface, a proximal surface, and said substantially flat lower surface; and said distal surface lies in a second plane adapted to be angled proximally relative to the first plane.

10. A loop electrode according to claim 2, wherein:

said cross section is defined by a convex upper surface and said substantially flat lower surface.

11. A loop electrode according to claim 1, wherein:

said substantially U-shaped member is made of one of chromium cobalt and carbonless stainless steel.

12. An electrocautery probe, comprising:

a) a pair of conductive arms having proximal and distal ends, said arms lying in a first plane and being joined to each other at their said proximal ends;

b) an electrode lead coupled to said proximal ends of said conductive arms and extending proximally therefrom; and c) a substantially U-shaped electrode having two upper ends, each of which is coupled to a respective one of said distal ends of said pair of conductive arms, said electrode having a cross section defining at least one sharp edge and a substantially flat lower surface.

13. An electrocautery probe according to claim 12, wherein:

said cross section defines a sharp distal edge and a sharp proximal edge.

14. An electrocautery probe according to claim 13, wherein:

said cross section is substantially triangular.

15. An electrocautery probe according to claim 14, wherein:

said substantially triangular cross section defines an acute triangle.

16. An electrocautery probe according to claim 14, wherein:

said substantially triangular cross section defines an obtuse triangle.

17. An electrocautery probe according to claim 13, wherein:

said cross section is defined by a distal surface, a proximal surface, and said substantially flat lower surface, said lower surface extending approximately 0.039–0.043 inches between said distal surface and said proximal surface.

18. An electrocautery probe according to claim 17, wherein:

said distal surface extends approximately 0.018–0.022 inches between said lower surface and said proximal surface.

19. An electrocautery probe according to claim 18, wherein:

said proximal surface extends approximately 0.063–0.067 inches between said distal surface and said lower surface.

20. An electrocautery probe according to claim 12, wherein:

said cross section is defined by a convex upper surface and said substantially flat lower surface.

21. An electrocautery probe according to claim 12, wherein:

said two arms of said probe lie in a first plane;

said cross section is defined by a distal surface, a proximal surface and said substantially flat lower surface; and said distal surface lies in a second plane which is angled proximally relative to said first plane.

22. An electrocautery probe according to claim 12, wherein:

said substantially U-shaped member is made of one of chromium cobalt and carbonless stainless steel.

23. An electrocautery probe according to claim 12, further comprising:

d) means for coupling said probe to a resectoscope.

24. An electrocautery probe according to claim 23, wherein:

said means for coupling comprises a mounting sleeve for sildeably coupling said probe to the resectoscope.

* * * * *